United States Patent [19]
Grobbee et al.

[11] Patent Number: 5,994,080
[45] Date of Patent: Nov. 30, 1999

[54] METHOD OF DIAGNOSING AN INCREASED RISK OF THROMBUS ASSOCIATED DISEASE BY DETECTING A CERTAIN T-PA POLYMORPHISM

[75] Inventors: Diederick Egberstus Grobbee, Delft; Cornelis Kluft, Sassenheim, both of Netherlands

[73] Assignee: Akzo Nobel, N.V., Netherlands

[21] Appl. No.: 09/029,023

[22] PCT Filed: Aug. 19, 1996

[86] PCT No.: PCT/EP96/03652

§ 371 Date: Feb. 20, 1998

§ 102(e) Date: Feb. 20, 1998

[87] PCT Pub. No.: WO97/07240

PCT Pub. Date: Feb. 27, 1997

[30] Foreign Application Priority Data

Aug. 21, 1995 [EP] European Pat. Off. .............. 95202248

[51] Int. Cl.$^6$ .............. C12Q 1/68; C12P 19/34; C07H 21/02
[52] U.S. Cl. ............. 435/6; 435/91.2; 435/91.1; 536/22.1
[58] Field of Search ................. 435/91.2, 91.1, 435/6; 536/22.1

[56] References Cited

FOREIGN PATENT DOCUMENTS

| WO 9521938 | 8/1995 | WIPO | ............ C12Q 1/68 |
| WO 8912697 | 12/1995 | WIPO | ............ C12Q 1/68 |

OTHER PUBLICATIONS

Iacoviello et al., *Fibrinolysis*, 8:1:49, 1994.
Ludwig et al., *Human Genetics*, 88:388–392, 1992.
Degen et al., *Journal of Biological Chemistry*, 261:15:6972–6985, 1986.
Iacoviello et al., *Fibrinolysis*, 10:Sup 2:13–16, 1996.
Bom et al., *Fibrinolysis*, 10:Sup 3:3, 1996.
Bom et al., *Circulation*, 92:8 (Sup 1):30–31, 1995.
van den Eijnden–Schrauwen et al., *Thrombosis and Haemostasis*, 74:4:1202, 1995.
Tishkoff et al., *Human Genetics*, 97:759–764, 1996.

*Primary Examiner*—Ardin H. Marschel
*Assistant Examiner*—Joyce Tung
*Attorney, Agent, or Firm*—Mary E. Gormley

[57] ABSTRACT

Blood clot formation is the key event in myocardial infarction. Besides increased coagulation, failure in blood clot lysis can induce undesired coronary thrombosis. Plasmin is essential for degradation of fibrin clots. Tissue-type plasminogen activator (t-PA) is the serine protease that converts plasminogen into plasmin. The association of the Alu insertion/deletion polymorphism in intron h of the t-pA gene to the risk of myocardial infarction was evaluated. Subjects with a documented history of myocardial infarction (n=162) and controls (n=258) were drawn from the Rotterdam Study, a population-based cohort study of 7983 subjects of 55 years or older. Allele frequencies were 0.54 for the insertion allele (t-PA Alu-h I) and 0.46 for the deletion allele, and were in Hardy Weinberg equilibrium. Among subjects that were homozygous for the insertion (n=138) were more than twice as many subjects with myocardial infarction compared to those homozygous (n=75) for the deletion (relative risk of 2.04, (95% CI 1.03–4.03), adjusted for age, gender, smoking, total cholesterol, HDL cholesterol, systolic and diastolic blood pressure and body mass index). Our results provide strong evidence for an association of a particular allele, t-PA Alu-h I, of the t-PA gene with the occurrence of myocardial infarction.

7 Claims, No Drawings

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

TCCGTAACAG GACAGCTCA                                                    19

(2) INFORMATION FOR SEQ ID NO:2:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

ACCGTGGCTT CAGTCATGGA                                                   20

METHOD OF DIAGNOSING AN INCREASED RISK OF THROMBUS ASSOCIATED DISEASE BY DETECTING A CERTAIN T-PA POLYMORPHISM

FIELD OF INVENTION

Blood clot formation is the key event in acute manifestations of vascular diseases like myocardial infarction, thrombi in peripheral blood veins and cerebral infarction. Apart from increased coagulation, failure in blood clot lysis can induce undesired coronary thrombosis. In many cases a longer or shorter period of time has been discerned during which the clot is formed and subsequently is dissolved prior to the permanent closure by the clot. During this phase of closure and reopening of blood vessels the clot dissolving or anticoagulant system, the fibrinolysis plays an important role. The exact nature is yet unclear, however in a definite infarction the clotting impulse has clearly been stronger than the reaction of the fibrinolytic system to react i.e. to dissolve the clot.

The proteolytic enzyme plasmin is essential for degradation of fibrin clots. Tissue-type plasminogen activator (t-PA) is a serine protease that converts plasminogen into plasmin. T-PA is widely accepted now as a therapeutic agent in the vast majority of cases of acute myocardial infarction[1]. When given in high doses it degrades occlusive thrombi promptly. T-PA is regarded as one of the most important activators of fibrinolysis and is known to have antithrombotic activity (There are numerous t-PA patent publications and other publications such as ref. 25 and 26 that illustrate this.)

Recent longitudinal studies have indicated that on the one hand decreased endogenous t-PA activity levels in plasma may be associated with increased risk of myocardial infarction in patients with angina pectoris[2], and with recurrent myocardial infarction[3]. On the other hand increased concentrations of endogenous t-PA antigen in plasma have also been associated with increased risk of recurrent myocardial infarction[4], cardiovascular events in patients with angina pectoris and coronary artery stenosis[5,6], and with risk of myocardial infarction in healthy males[7]. It has been suggested in support of the latter that the significant positive association between concentrations of t-PA antigen and the inhibitor, of free t-PA, the socalled plasminogen activator inhibitor (PAI-1) antigen[8], reflects that increased concentrations of t-PA antigen can also reflect circulating t-PA/PAI-1 complex to a large degree. Thus a high concentration of t-PA antigen could indicate a reduced rather than an enhanced fibrinolytic activity. The increase in production of t-PA inhibitor, PAI-1 could largely neutralize t-PA activity. Thus although an increase in the t-PA concentration would largely be attributed to the inactive complex of t-PA-PAI-1 in this manner increased PAI-1 could manifest itself and thus become the actual cause of the risk. Indeed increased plasma concentrations and PAI-1 activity have been indicated as predictive of risk. Recently heredity for increased PAI-1 has also been indicated as predictive of risk. Eriksson P.[24] et al. e.g. describe genotyping for the 4G/5G polymorphism in the PAI-1 promoter region with an allele specific oligonucleotide melting technique known per se. The 4G allele was associated with a higher plasma PAI-1 activity. Thus this group provided evidence for an independent etiological role of PAI-1 in myocardial infarction.

In Iacoviello L. et al [23] an association between family history of thrombosis and acute myocardial infarction (AMI) has been suggested. Moreover, changes in fibrinolysis are suggested as being correlated with the risk of ischemic vascular disease. T-PA levels in a group of patients with AMI, selected from the GISSI-2 study population were studied. Patients with a family history of thrombosis (at least two first degree relatives affected by MI and/or stroke before 65 years) were studied in parallel with MI patients with no family history of thrombosis 6 months after the AMI episode. The results of the study were that the levels of t-PA antigen in the group with family history of thrombosis (10.1±6 ng/ml, mean±SE.n=53) did not differ significantly from the levels in the group without family history (10.4±0.6 ng/ml, n=53). Curiously in contrast, when patients with only family history of MI were considered, t-PA antigen levels were significantly lower than in the respective control group (7.5±4.4 vs 11.1±3..5 ng/ml, t=2.6. p<0.02. n=16). No differences were observed in t-PA and PAI activity and in PAI-I antigen levels, among all studied groups.

An insertion/deletion (I/D) polymorphism in intron h of the t-PA gene in the AMI population was studied by Iacoviello et al. Preliminary data showed that the frequencies of both alleles were respectively 0.51 and 0.49 and the genotype distribution was in Hardy-Weinberg equilibrium. The I/D polymorphism was associated with t-PA activity levels (p<0.03), not with t-PA antigen concentrations. The D allele was associated with higher levels of t-PA activity. Curiously in conclusion, decreased antigen levels of t-PA were found in association with family history of AMI. This marker seemed to be differently expressed in patients with family history of thrombosis in different vascular districts.

It is apparent from the above that plasma levels of t-PA and PAI-1 may provide only limited and puzzling information. The data show associations between increased t-PA antigen and the risk of ischemic events in population studies, while in families with a family history of myocardial infarction t-PA antigen is lower. Iacoviello does not find a relationship between disease and genetics. The frequency of D and I allele in myocardial patients with and without family history does not differ. Apparently the results of family studies cannot be compared to population studies. Another problem with this study is the fact that the analysis revealing an association of the D allele with a higher t-PA activity without consequence for the t-PA antigen was carried out in all AMI patients i.e. with and without family AMI/thrombosis. As the t-PA antigen differs for these groups the results are discutable due this mix of patients. Besides the moot assumption that a local process could be observed in plasma, there is another pitfall in using plasma levels when studying the association between the fibrinolytic system and arterial disease. True plasma levels of t-PA antigen and activity are, like many other haemostatic factors, difficult to measure. They are influenced by many other parameters, especially PAI-1[9]. This limits the possibility to examine the role of fibrinolytic parameters when the development of arterial disease is studied. An alternative approach is thus required to analyse potential parameters associated with increased risk of vascular diseases.

An alternative approach is that of genetics. Genotypes are reliably and relatively easily measured, and are not influenced by external factors. Current technology offers a broad scope of reliable techniques for detection and analysis of anomalies in the genetic make up. In particular a number of diagnostic methods on the basis of nucleic acid analysis are known for various diseases. For more than 100 diseases, the disease mutation can be revealed by DNA-diagnostic techniques. Examples are Cystic Fibrosis, Duchene Muscular Dystrophy, Huntingtons Disease and the Factor V Leiden mutant Factor V associated with thrombolytic disease (PCT EP95/00553).

An Alu insertion/deletion (I/D) polymorphism was identified in 1991 for the intron h of the t-PA gene using polymerase chain reaction and direct sequencing[10]. The minor 655 bp allele is the result of a deletion of the entire first Alu sequence located in intron h. The mechanism of slipped mispairing is given as hypothetical process of formation of this allele. The t-PA Alu associated RFLP can be immediately visualised by loading the PCR products on an agarose gel and subsequent ethidium bromide staining. The polymorphic fragments within the human t-PA gene could be detected in EcoRI, XmnI and TaqI digests. The sequence of the human t-PA gene fragment 25.201–26.200 comprising the two Alu inserts in intron h and exon IX is provided. The first Alu insert is located at 25.272–25.573. The second Alu insert is located at 25.762–25.927. Exon IX is located at 25.941–26.025. The organisation of the gene is described as being that of Degen et al[27]. This article also describes "it is noteworthy that Alu recombination events as a cause of hereditary t-PA deficiency have not been observed so far, although a large number of Alu copies is distributed throughout this gene. This is contrary to the frequent observation of Alu-mediated rearrangements in globin genes and the low density lipoprotein receptor gene." Nothing is mentioned regarding any diagnostic use of such polymorphism. The article is concerned with the actual phenomenon and the manner in which it arises. Nothing is stated with regard to function of the mutation.

A further recent publication on the phenomenon of Alu repeats[29] reveals that a typical Alu element is 282 nucleotides long and comprises two subunits rich in GC connected by an adenine rich linker with the sequence ending in a polyadenyl tail. Approximately 700.000 copies of Alu elements per human haploid genome is predicted. In practice Alu elements are found in the introns of almost all known protein encoding genes. The dispersion of repetitive sequence elements is a source of genetic variability that contributes to genome evolution. It is suggested Alu repeats may cause genetic diseases by a number of mechanisms such as de novo Alu insertions and splicing of intragenic Alu elements into mRNA. An analysis of known protein coding regions revealed 17 Alu inserts in 15 coding sequences. In three events these caused genetic diseases. No relevance of Alu elements in introns other than the evolutionary one is taught or suggested. The article is concerned with Alu insertions in exons i.e. the coding portion of nucleic acid.

SUMMARY OF THE INVENTION

Quite unexpectedly upon studying t-PA Alu I/D polymorphism in survivors of myocardial infarction we have found a relation between the t-PA Alu-h I allele and coronary heart disease. Apart from the reasons given above the relevance hereof is surprising as there are 28 Alu sequences in the t-PA gene. No relevance has been attached to any of these sequences previously (Degen et al. 1986).

DETAILED DESCRIPTION OF THE INVENTION

This has thus opened the way to a test that may have diagnostic value in identifying individuals or groups of individuals with an abnormally increased risk of diseases associated with thrombus formation. Such diseases include myocardial infarctions, cerebral infarctions, peripheral thrombi, transient ischemic attacks, dementia and thrombosis. Any method known per se for detecting the presence of the t-PA Alu-h I allele can be used for identifying a person or group of persons at risk of disease associated with thrombus formation in a method according to the invention. More especially a method whereby the functional mutation in the allele responsible for the increased risk of ischemic events that is physically correlated with the presence of the Alu repeat insert in intron h of the t-PA gene is detected falls within the scope of the subject invention.

This method in one embodiment involves analysis of a nucleic acid sequence of a subject to be tested for the presence or absence of the t-PA Alu-h I allele or a part of said allele of the person to be tested, said part being a part within which the Alu insert can be located.

As an alternative the method comprises determination of the presence or absence of the functional mutation in the allele responsible for the increased risk of ischemic events that is physically correlated with the presence of the Alu repeat insert in intron h of the t-PA gene.

Naturally the method according to the invention may also comprise both the above mentioned embodiments in combination.

The method according to the invention can for example comprise amplification of the nucleic acid of the person to be tested in a manner known per se. The amplification reaction can comprise amplification of DNA or amplification of DNA in combination with RNA or simply comprise amplification of RNA. When using an amplification reaction wherein both DNA and RNA could be amplified one can destroy the DNA using DNase in a manner known per se prior to the amplification or one can select the amplification primers such that the amplified DNA and amplified RNA differ in length and composition due to the presence and absence of introns in order to discern between amplified chromosomal nucleic acid and nucleic acid amplified from mRNA. When using an ELGA detection method for example the difference in length of the amplified products should be at least 45 nucleotides. Therefore, the amplified sequence must comprise at least one exon-exon junction in order to discern between the amplified chromosomal nucleic acid and nucleic acid amplified from mRNA if detection of mRNA is required rather than of the genomic nucleic acid. As NASBA is a nucleic acid amplification method especially suited for RNA targets use of the NASBA amplification method is considered to be a preferred embodiment for carrying out the method according to the subject invention when mRNA is to be analysed. A preference for NASBA exists in some cases due to the fact that it is especially suited for RNA targets and amplification of intracellular RNA, such as ribosomal RNA or messenger RNAs from the cell itself. This method will be applicable when the functional mutation in the allele responsible for the increased risk of ischemic events that is physically correlated with the presence of the Alu repeat insert in intron h of the t-PA gene lies within the coding nucleic acid. For genomic DNA any of the known amplification methods will suffice. There are a number of target amplification reactions that are generally carried out in the state of the art comprising NASBA (Nucleic Acid Sequence Based Amplification) PCR (Polymerase Chain Reaction), LCR (Ligase Chain Reaction) and RCR (Repair Chain Reaction). The amplification can for example suitably occur by the well established technique of PCR as is illustrated in the Example. Such target amplification reactions are well known to a person skilled in the art. It is required to use one or more primers specific to recognize and hybridize to stretches of nucleic acid adjacent to the 5' and 3' end of the stretch of nucleic acid in which the mutation can be located, said hybridisation being to a degree sufficient for amplification of the stretch of nucleic acid in which the mutation can be located. The stringency of hybridisation required is also known to a person skilled in the art of target amplification of nucleic acid. For PCR target amplification methods the Amplicor® reaction kits are commercially available. It is also possible to use a primer sufficiently specific to recognize and hybridize to the stretch of nucleic acids in which the mutation itself can be located.

The nucleic acid sequence of a human t-PA gene has been determined by Degen et al. Using the nucleic acid sequence for hybridisation comprising at least a part of intron h it is quite simple to isolate and/or amplify and/or subsequently detect a mutation present in the t-PA gene. Further primers of nucleic acid sequences for hybridisation and/or amplification purposes can be selected to hybridise with the t-PA sequence. It lies within the reach of a person skilled in the art to select oligonucleotide sequences best suited to isolate and/or amplify and/or determine the presence and nature of the mutation he is screening for in a method according to the invention as the sequence of the t-PA gene is known.

The method according to the invention in any of the embodiments disclosed above subsequently also comprises a detection step of the amplified sequence. The detectable marker that can be used will depend on the particular embodiment selected. The detectable marker will recognize a sequence located somewhere between the two recognition sites of the primers used in the amplification reaction. Such a detectable marker can be a sequence, capable of hybridizing specifically to a part of the amplified sequence. In one embodiment of the method according to the invention preferably, either one of the primers employed or the detectable marker will be capable of specifically recognizing a part of the nucleic acid sequence of the relevant Alu repeat in intron h of the t-PA gene or any other marker or mutation by which the allele (Alu-h I) can be distinguished from other alleles. Preferably one of the primers at least and/or the detectable marker will then also be specific for a part of the amplified sequence upstream or downstream of the relevant Alu repeat insertion in intron h of the t-PA gene.

In an alternative embodiment as such or in combination with the above mentioned embodiment the detectable marker will recognize a sequence located somewhere between the two recognition sites of the primers used in the amplification reaction. The detectable marker that can be used can be a sequence, capable of hybridizing specifically to a part of the amplified sequence. In one embodiment of the method according to the invention preferably, either one of the primers employed or the detectable marker will be capable of specifically recognizing a part of the nucleic acid sequence, said part comprising the relevant functional mutation in the allele responsible for the increased risk of ischemic events that is physically correlated with the presence of the Alu repeat insert in intron h of the t-PA gene. The functional mutation should be located within 1000 kb of the Alu marker in intron h as it must be physically linked to the marker. It must be present on the same chromosome. It need not necessarily be present in the t-PA gene. It also need not necessarily be associated with the coding region of the t-PA gene or other gene located within 1000 kb of the t-PA gene. Preferably one of the primers at least and/or the detectable marker will be specific for a part of the amplified sequence upstream or downstream of the location of the relevant mutation.

After amplification of the nucleic acid, analysis of the amplified nucleic acid in a manner known per se for detecting the presence and optionally the nature of the mutation is to be carried out in the method according to the invention. After the amplification step the resulting nucleic acid sequence can be compared with a normal sequence or a sequence known to carry the mutation, thereby ascertaining the presence or absence of the mutation, with the presence being indicative of an increased risk of a thrombus associated disease. The sequence to be detected may be comprised within the coding sequence of the t-PA gene or may also be comprised elsewhere on the t-PA Alu-h I allele. Detection of the presence of the I allele is sufficient to diagnose an increased risk of thrombus associated disease, but preferably the functional mutation responsible for the increased risk for ischemic disease that is physically linked to the Alu I presence will be detected.

Amplification using primers capable of hybridising to the nucleic acid sequence of the allele located on each side of the mutation to be detected can be used to carry out the method according to the invention in a manner known per se for diagnostic tests based on detection of the presence or absence of a specific mutation in the nucleic acid to be amplified. The primers used by Ludwig et al suffice to detect both D and I intron h Alu alleles. Any primers located to the 5' side of the 5' primer according to Ludwig and any 3' primer located to the 3' side of the 3' primer according to Ludwig should also suffice. A person skilled in the art of amplification will be able to devise suitable primers on the basis of the sequence data known. In the Example we have used similar primers to those used by Ludwig and the primers used correspond to parts of the partial sequence of the t-PA allele used by Ludwig et al.

In the case of the functional mutation being located in the coding part of nucleic acid the analysis need not be restricted to assessment of genomic nucleic acid but can comprise analysis of mRNA in a manner known per se.

It has become possible to use DNA techniques or to use antibodies for determining the presence of mutant nucleic acid sequences or proteins when screening for the mutated allele or expression products thereof comprising the functional mutation physically linked to the insertion of the Alu repeat of intron h of the t-PA gene. The subject invention is therefore directed at a method for screening for the presence of a genetic defect associated with increased risk of thrombus associated disease, said method comprising determination of the presence of a mutation in the nucleic acid material of the allele in a manner known per se or in the expression product of said allele, by analysis of said expression product or analysis of a proteolytic fragment of said expression product in a manner known per se. The analysis according to the subject method can therefore be carried out at nucleic acid level e.g. at DNA and/or mRNA level of the allele and at protein level on any of the expression products of the allele.

The method according to the invention is directed at detecting one or more mutations in the allele comprising the functional mutation or the expression products thereof at either nucleic acid or protein level or both.

As stated above the method according to the invention can also be carried out by analysing the protein rather than the nucleic acid sequence encoding the protein. When the detection of the mutated protein occurs by using a specific antibody it is possible to use an antibody specifically directed against expression product comprising the mutation for detection of the presence and optionally the nature of the mutation. Alternatively it is also possible to proteolytically cleave the protein to be analysed, thereby obtaining linear or partially linear structures making it possible to use antibodies specific for the mutation in the primary nucleic acid sequence of the expression product.

A further possibility for detection of the mutation lies in the older technique of amino acid sequence analysis. Once the amino acid sequence of the non-mutated expression product is known it is quite simple to determine the amino acid sequence of the factor to be analysed and compare that sequence to the known sequence of the corresponding non-mutated factor. However, using antibodies is a simple and efficient way to analyse proteins for the presence of mutations, for example using ELISAS or RIAS or variety of other immunological tests known to a person skilled in the art.

For detecting the mutation one can use a specific antibody capable of binding to the mutant expression product or of binding to a linear proteolytic fragment of the mutant expression product comprising a mutation, said antibody having a lower binding affinity for the non-mutated expression product or for the corresponding proteolytic fragment of the non-mutated expression product.

It is also possible as an alternative to use an antibody capable of binding to a non mutated expression product, said antibody having a lower binding affinity for the corresponding expression product and/or for the proteolytic fragment thereof comprising a mutation In this instance a test can be developed whereby non-binding of the antibody to the isolated protein or proteolytic fragment is illustrative of the presence of a mutation.

The methods to be used will depend on the circumstances of the case and also the objective of the test. For example when screening a large population the cheapest method to be used will be preferred. In some instances the mutation to be detected will be difficult to determine using antibodies and then use of nucleic acid sequences or restriction fragment analysis can be preferred. Also if the enzyme to be used for a restriction fragment test is inexpensive then carrying out such a test is very simple and cheap to carry out and will obviously be suitable.

The invention is also directed at kits comprising the elements necessary for carrying out the method according to the invention in all the embodiments illustrated. This comprises for example test kits comprising one or more of the specific antibodies described above and/or comprising one or more primers or pairs of primers for target amplification reactions and/or hybridisation reactions as described above. Specifically the invention is directed at a kit comprising a primer or primers for amplifying the nucleic acid sequence comprising the mutation of the nucleic acid sequence due to the presence of the Alu repeat in intron h of the t-PA gene. The kit can comprise primers and/or antibodies for the detection of one particular mutation or for a number of mutations.

It is possible to determine the presence or absence of a mutation in a method according to the invention without amplification of the nucleic acid material. There are a number of techniques known to a person skilled in the art that were used before the target amplification reaction was developed for determining the presence of mutations on nucleic acid and these can all be used in various embodiments of the method according to the invention. For example the mutation to be determined can be detected by a hybridisation reaction to at least one nucleic acid sequence sufficiently specific to hybridise to at least part of the nucleic acid sequence encoding the factor to be analysed followed by analysis of the nucleic acid thus isolated in a manner known per se for detecting the presence and optionally the nature of the mutation.

The detection of the presence and optionally the nature of the mutation can occur by subjecting the nucleic acid thus isolated to sequence analysis by using for example the Sanger sequence reaction to ascertain the nucleic acid sequence and subsequently to compare the results of this sequencing with the sequence known for either the non-mutated factor or the mutated factor. It is also possible to subject the nucleic acid sequence isolated to a further hybridisation test. The further hybridisation test being carried out with a stretch of nucleic acid material with a corresponding complementary sequence of sufficient length and specificity to at least hybridize to a fragment of the nucleic acid material comprising the mutation to detect the presence and optionally the nature of the mutation. The first hybridisation step merely isolates nucleic acid encoding the factor whether this is mutated or not and the second hybridisation step actually comprises hybridising the isolated sequence to the complementary sequence of the actual mutated nucleic acid sequence one wishes to ascertain in order to determine the presence or absence of said mutation on the isolated nucleic acid material. This latter hybridisation reaction should be carried out under stringent conditions for reliable results. Thus two classical methods for determining the presence of a mutation on a particular nucleic acid are hereby illustrated and it will be obvious to a person skilled in the art that a number of known techniques can be used. In various standard books for biochemistry such techniques are amply illustrated for example in a handbook of molecular cloning (e.g. Sambrook et al. (Sambrook, J. Fritsch, E. F., Maniatis T. (1989) Molecular Cloning. A laboratory manual. Second ed. Cold Spring Harbor Laboratory Press, Cold Spring Harbor, N.Y.)) Maniatis a Laboratory Manual for Molecular Cloning. It is also possible to analyse the amplified nucleic acid material obtained in the screening method according to the invention by using subsequent analysis tests using sequencing reactions or hybridisation to a corresponding complementary sequence of sufficient length and specificity to at least hybridize to a fragment of the nucleic acid material comprising the mutation to detect the presence and optionally the nature of the mutation as was illustrated above for analysis of isolated nucleic acid material that had not been subjected to an amplification reaction.

Alternatively the analysis of isolated and optionally amplified nucleic acid material can comprise RFLP testing in a manner known per se. Due to the differences in restriction fragment lengths of nucleic acid of the allelic forms gel electrophoresis and staining e.g. with ethidium bromide of isolated and optionally amplified nucleic acid will provide bands at different heights on the gel. In the case of the Alu I/D polymorphism of intron h of the t-PA gene the presence of a larger fragment corresponds to the I allele and a smaller fragment corresponds to the D allele when the method according to the invention comprises determination of the presence or absence of the Alu insertion in intron h of the t-PA gene using standard RFLP techniques. This principle is illustrated in the Ludwig et al reference and in the Example.

The method according to the invention can be applied to isolation of total nucleic acid from cultured cells, isolation of total nucleic acid from blood, isolation of total nucleic acid from cervical scrapings.

The requirements to be made for the oligonucleotide primers and detectable marker to be used in the amplification reaction of the method according to the invention will be obvious to a person skilled in the art. The normal requirements for amplification reaction primers and markers regarding degree of homology and applied hybridisation conditions are in force. This means in general terms a primer will comprise at least 10 nucleotides capable of hybridising to a corresponding part of the sequence to be amplified under normal to stringent conditions. The requirements can be found in a handbook of molecular cloning (e.g. Sambrook et al. (Sambrook, J. Fritsch, E. F., Maniatis T. (1989) Molecular Cloning. A laboratory manual. Second ed. Cold Spring Harbor Laboratory Press, Cold Spring Harbor, N.Y.)). In a preferred embodiment the oligonucleotide probe will be selected to exhibit a degree of homology ensuring the most reliable result at a reasonable cost. Optimum results are in general obtained when the homology is 100% and the oligonucleotide probe has a length of 15 to 25 oligonucleotides. When using NASBA the amplified sequence i.e. the product is the complementary strand, thus the oligonucleotide for detecting the amplified product will correspond to the sequence of the original nucleic acid. When using PCR the amplified sequence i.e. the product is a double stranded DNA and detection can occur of either strand. Thus the oligonucleotide used for detection of amplified product may hybridize to either the coding strand or the complementary strand of nucleic acid to be amplified. We hereby cite some general references illustrative of the PCR methodology. The content thereof related to carrying out PCR reactions is hereby enclosed (PCR Technology, J. A. Ehrlich, ed., Stockholm Press, New York (1989); Molecular Methods for Virus Detection, D. L. Wiedbrauk and D. H. Farkas, eds., Academic Press, New York (1995). Nucleic Acid Hybridisation, B. D. Hames and S. J. Higgins, eds., IRL Press, Oxford, Washington, D.C. (1985).

The invention is also directed at a diagnostic kit for determining whether an individual or a group of individuals has an increased risk of thrombus associated disease, said kit comprising at least one pair of oligonucleotide primers, said primers being capable of amplifying nucleic acid of a t-PA allele of a eukaryotic species in a manner known per se and/or said primers being capable of amplifying nucleic acid comprising the functional mutation in the allele responsible for the increased risk of ischemic events that is physically correlated with the presence of the Alu repeat insert in intron h of the t-PA gene, said eukaryotic species preferably being a human being. Such a kit will further comprise a detectable marker of the amplified sequence. The detectable marker of the kit according to the invention or for use in the method according to the invention can suitably be an oligonucleotide sequence capable of hybridizing to the amplified sequence. The detectable marker can also be an antibody capable of specifically recognizing the amplified sequence. The detectable marker can be provided with a label that is detectable as is common in the state of the art for markers of nucleic acid sequences, e.g. an enzyme, a chromogenic substrate, a radio isotope, a fluorescent group etc. Also the detectable marker can be capable of specifically immobilizing the amplified sequence in a manner known per se followed by detection of the immobilized amplified sequence in a manner known per se with or without a rinsing step and using a further compound binding to the immobilized sequence and subsequently providing a detectable signal. The execution of this type of tests is routine to a person skilled in the art of nucleic acid detection. The kit will comprise primers and detectable marker in a combination such that either only the amplified sequence to be detected is present in the sample or else a combination of amplified sequences is present but the detectable marker will only detect the amplified sequence to be detected. The combinations that are suitable can easily be ascertained upon comparison of the nucleic acid sequences known for the alleles to be detected or the specific parts thereof that are to be detected and more specifically upon comparison of the various sequences for the t-PA alleles, in particular of the relevant parts of the sequences of the intron h Alu I and D alleles.

In particular when a kit according to the invention is to be used for amplifying both DNA and RNA the pair of oligonucleotide primers is selected such that the amplified sequence comprises at least one exon-exon junction. A diagnostic kit according to the invention for determining whether an individual or a group of individuals has an increased risk of thrombus associated disease will comprise one or more primer pairs for amplifying nucleic acid comprising the region where the mutation is to be expected when present. Any other components normally required for such an amplification reaction may also be included such as probes for detection of the amplified nucleic acid. The amplification can be PCR, NASBA or any other nucleic acid amplification reaction known to a person skilled in the art. The manner in which such amplification reactions are to be carried out is analogous to those of other diagnostic tests requiring amplification and will be obvious to a person skilled in the art on the basis of general knowledge concerning the techniques and the nucleic acid sequence of the various alleles for the gene of interest in particular of the allele comprising the functional mutation and has been elucidated elsewhere in the description.

A diagnostic kit for determining whether an individual or a group of individuals has an increased risk of thrombus associated disease in a method according to the invention is also claimed, said kit comprising a detectable marker enabling RFLP fragment size analysis i.e. to ascertain whether the tested nucleic acid is of the I allelic form with an Alu insertion in the h intron of the t-PA gene and/or to ascertain whether the tested nucleic acid comprises the functional mutation physically linked to the presence of the Alu insert in intron h of the t-PA gene and responsible for the increased risk of thrombus associated disease.

A diagnostic kit for determining whether an individual or a group of individuals has an increased risk of thrombus associated disease in a method according to the invention is also claimed, said kit comprising a detectable marker for a functional mutation physically associated with the presence of an Alu insertion in intron h of the t-PA gene. Such a diagnostic kit can suitably comprise a detectable marker for the presence of the Alu repeat in intron h of the t-PA gene. Such a detectable marker can easily be derived by a person skilled in the art to specifically recognise the relevant part of intron h. The detectable marker may also specifically recognise the sequence comprising the functional mutation associated with the insertion in intron h. For a diagnostic kit directed at carrying out RFLP the detectable marker may be a fragment of nucleic acid having a length corresponding to the length of the fragment expected for the fragment comprising the mutation.

On the basis of ascertaining the presence of the mutation it subsequently becomes possible to select individuals for an intensified preventive regime or specific antithrombotic treatment of acute vascular diseases.

The following example illustrates how the link between the Alu insertion in the t-PA gene and the increased risk of thrombus associated disease was obtained.

In addition to the methods of detection an allele responsible for the increased risk of thrombus associated disease as such is also considered to fall within the scope of the invention. Such an allele must be physically associated with the presence of an additional Alu marker in intron h of the t-PA gene and such an allele comprises the functional mutation responsible for the increased risk. Such an allele is located in the genomic nucleic acid within 1000 kb of the Alu-h-I-t-PA allele. The allele claimed according to the invention does not comprise the nucleic acid sequence according to Ludwig et al. Use of the allele according to Ludwig et al in a method according to the invention does fall within the scope of protection.

EXAMPLE

Methods

Population

The Rotterdam Study is a population based study of 7983 subjects aged 55 years and over. Between March, 1990 and July, 1993 all subjects aged 55 years and older, living in Ommoord, a suburb of Rotterdam, The Netherlands, were invited to participate. The overall response rate was 78%. The rationale and design of the study have been described elsewhere[1].

Selection of Cases and Controls

Case patients (n=162) were selected from participants of the Rotterdam Study based on the presence of an infarction on the ECG, using the diagnostic classification system of the Modular ECG Analysis System[12], independent of a history of chest pain; control subjects (n=258) were drawn from the same five year age strata where the cases of myocardial infarction were found and constituted a sample of study participants who had no history of cardiovascular disease, i.e. no history of myocardial infaction, angina pectoris, stroke, a normal ECG and no peripheral arterial disease (ankle/arm index >0.9)[13]. Inclusion criterium for all subjects was the availability of a blood sample.

Measurements

Subjects were all visited at home. Information on current health status, medical history (including myocardial infarction and stroke), drug use, and smoking behaviour was obtained by a computerized questionnaire, which included the Dutch version of the Rose cardiovascular questionnaire[14]. The home interview was followed by two visits at the research centre. During those visits several cardiovascular risk indicators were determined. Height and weight were measured, and body mass index was calculated (in kilograms per meter squared). Sitting blood pressure was measured at the right upper arm with a random zero sphygmomanometer. The average of two measurements obtained at one occasion was used. Systolic blood pressure at the ankles (posterior tibial artery) was measured in semisupine (±45%) position with an adult size regular cuff just above the malleoli, and a 8 MHz Doppler transducter[15]. The ankle/arm index is the ratio of the systolic blood pressure at the ankle to the systolic pressure of the arm. Peripheral arterial disease was defined as a right or left ankle/arm index lower than 0.9. Blood sampling and storage were described elsewhere[16]. Serum total cholesterol was determined with an automated enzymatic procedure[17]. High density lipoprotein cholesterol concentration was measured similarly, after precipitation. After the gene was cloned, an insertion/deletion (I/D) polymorphism resulting from the presence/absence of an Alu repeat in the 8th intron of the t-PA gene was identified in all 420 subjects.[18]

Statistical Analysis

Means and proportions of potential confounders were calculated for all three genotypes and differences between groups were tested with analysis of variance. The relative risk of myocardial infarction (estimated as the odds ratio) for those heterozygote and homozygote for the insertion compared to those homozygous for the deletion, was calculated using logistic regression. Multivariate logistic regression was used for adjustment for potential confounders such as age, gender, total and HDL cholesterol, body mass index, systolic and diastolic blood pressure and smoking. Results are presented with a 95% confidence interval. To estimate the proportion of cases of myocardial infarction that may be attributed to the t-PA gene polymorphism (population attributable risk) we used the method as described by Miettinen[19].

The amplification of the 967/655 bp fragments of the t-PA gene was performed essentially as previously described using as 5' primer 5'-TCCGTAACAGGACAGCTCA-3' (Sequence id no 1=nt 25.216–25.234) (from Isogen) and as 3' primer 5'ACCGTGGCTTCAGTCATGGA-3' (Sequence id no 2=nt 26.181–26.162) (from Isogen). The amplification comprises subjecting 50 microliters of a mixture containing 20 mM TRIS-HCl (from Gibco BRL), pH 8,4, 50 mM KCl, 1 mM $MgCl_2$ (from Gibco BRL), 0.05% (v/v) detergent (polyoxyethylene ether) (min 99.5%) (from Gibco BRL), 0.05% DMSO (from Merck), 0.2 mM of each nucleoside triphosphate (from Pharmacia), 100 ng of each primer, 100 ng DNA and 1 U Taq polymerase (Gibco BRL) to denaturation for 4 min. at 94° C., followed by 32 cycles of 94° C. (1 min.), 58° C. (1.5 min.), 72° C. (2 min.), followed finally by 4 min. at 72° C. The PCR apparatus used was HYBRID Omnigene of Biozym. 20 microliters of the PCR products with 2 microliters of SLM loading mix were separated on a 2% agarose gel (pronarose gel) at 100V/500 mA. Identification of fragments can be caried out with a marker with 100 bp ladder.

Results

Complete data were available for 162 case and 258 control subjects. Selected baseline characteristics of the study population are given in Table 1. No significant differences in cardiovascular risk factors between the groups classified by different genotypes were found. Among the control subjects the allele frequencies were 0.46 for the allele with the deletion and 0.54 for the alleles with the insertion and were in Hardy-Weinberg equilibrium. The crude and adjusted relative risks of non-fatal myocardial infarction are presented in Table 2. The relative risk of myocardial infarction for subjects homozygous for the insertion to those homozygous for the deletion was 2.04 (1.03–4.03), adjusted for age, gender, smoking, body mass index, systolic, and diastolic blood pressure, total and HDL cholesterol. The adjusted relative risk for heterozygous subjects was 1.42 (95% CI 0.74–2.73). Of all cases of myocardial infarction 33% was estimated to be attributed to either homo- or heterozygosity for the insertion.

Discussion

We provide evidence that polymorphic variation of the t-PA gene is strongly associated with the risk of non fatal myocardial infarction, independent of other risk factors. As t-PA plays an essential role in the degradation of intra-arterial fibrin clots, this association most likely reflects a genetically determined impaired capacity of the fibrinolytic system to respond adequately to coronary thrombosis in myocardial infarction. To our knowledge this is the first study to investigate an association between the t-PA gene and myocardial infarction. It is unlikely that population heterogeneity could explain our results. Cases and controls were drawn from a single-centre population-based study among 7983 subjects. All subjects participating in our study were caucasians and allele frequencies did not differ from those observed by others[20].

A limitation of our study is its restriction to non-fatal myocardial infarctions, by nature of its cross-sectional design. However, it is assumed that the t-PA gene does not influence the fatality of a myocardial infarction. T-PA is supposed to have its effect via impaired coronary clot lysis and an effect of impaired t-PA activity would increase rather than decrease the risk of a fatal myocardial infarction, and thus the observed association may reflect an underestimate of the true association. Even though we identified the association between the t-PA gene and non-fatal myocardial infarction, the mechanism behind the increased risk remains unknown. Apart from its major importance in fibrin clot dissolution t-PA also plays a role in various other cellular processes including cell migration[21,22]. In several studies increased t-PA antigen and decreased t-PA activity in plasma have been associated with increased risk of myocardial infarction[4,6,7,2]. The nature of the polymorphism, insertion or deletion of an Alu repeat in intron h, makes a direct functional effect of the polymorphism on the fibrinolytic balance unlikely. Rather the Alu repeat insertion may be closely physically linked to a mutation that does have an unknown functional effect either in or close to the t-PA gene and thereby increases the risk of myocardial infarction. In or close to the t-PA gene implies within 1000 kb of the t-PA gene. This functional effect may reside locally or systemically.

Our findings may be of great public health importance. As the prevalence of the t-PA I allele is high this variant of the t-PA gene may play a role in a high percentage of myocardial infarctions in the population. It is estimated that in 33% of cases myocardial infarction may be attributed to carriage of the t-PA I allele.

Thus the presence of the t-PA I allele increases the risk of myocardial infarction by 42% for heterozygotes and with more than a factor two for homozygotes. Some 33% of all (non-fatal) cases of myocardial infarction may at least in part be attributed to the t-PA I allele.

References

1. GUSTO Circulation 1994; 90(6):2658–65

2. Munkvad S, Gram J, Jespersen J. A depression of active tissue plasminogen activator in plasma characterizes patients with unstable angina pectoris who develop myocardial infarction. Eur. Heart J. 1990;6:525–8.

3. Gram J. Jespersen J. A selective depression of tissue plasminogen activator (t-PA) activity in euglobulin characterizes a risk group among young survivors of acute myocardial infarction. Thromb Haemostas 1987; 57:137–9.

4. Gram J. Jespersen J. Kluft C. Rijken DC. On the usefulness of fibrinolysis variables in the characterization of a risk group for myocardial reinfarction. Acta Med Scand 1987; 221:149–53.

5. Hanson J H, Olofsson B O, Nilsson T K. Predictive value of tissue plasminogen activator mass concentration on long term mortality in patients with coronary artery disease. A 7 years follow-up. Circulation 1993, 88:2030–34.

6. Thompson S G, Kienast J. Pyke S D M, Haverkate F. van de Loo J C W for the ECAT study Group. Hemostatic factors and risk of myocardial infarction or sudden death in patients with angina pectoris. N. Engl. J. Med. 1995; 332:635–41.

7. Ridker P M. Vaughan D E, Stampfer M J. Manson J E, Hennekens C H. Endogenous tissue-type plasminogen and risk of myocardial infarction Lancet 1993;341:1165–8.

8. Chandler W L, Trimble S L, Loo S C, Mornin D. Effect of PAI-1 levels on the molar concentrations of active tissue plasminogen activator and t-PA/PAI1 complexes in plasma. Blood 1990;76:930–7.

9. Kluft C. Constitutive synthesis of tissue-type plasminogen activator and plasminogen activator inhibitor: conditions and therapeutic targets. Fibrinolysis 1994;8(Suppl):1–7.

10. Ludwig M. Wohn K D, Schleuning W D, Olek K. Allelic dimorphism in the human tissue-type plasminogen activator (TPA gene as a result of an Alu insertion/deletion event. Hum Genet 1992;88:388–92.

11. Hofman A, Grobbee D E, de Jong P T V M, van den Ouweland F A. Determinants of disease and disability in the elderly: the Rotterdam Elderly Study. Eur. J. Epidemiol 1991;7:403–22.

12. Methodology of the Modular ECG Analysis System MEANS. Bemmel J H van, Kors J A, Herpen van G. Meth Inform Med. 1990;29:346–353.

13. Vogt J. Clin Epidemiol

14. Rose G A, Blackburn H. Gillum R F. Cardiovascular survey methods. World Heath Organization, Geneva, Switzerland 1982.

15. Bots M L, van Swieten J C, Breteler M M, de Jong P T V M, van Gijn J. Hofman A, Grobbeee DE. Cerebral white matter lesions and atherosclerosis in the Rotterdam Study. Lancet 1993; 341:1232–37.

16. Bom van der J G, Bots M L, de Bruijn A M, Hofman A, Grobbee D E. Measurement of β-thromboglobulin in the elderly. Findings from the Rotterdam Study. Fibrinolysis 1994;8 (Suppl 2):157–9.

17. Vangent C M, Vandervoort H A, De Bruijn A M. Cholesterol determinations. A comparative study of methods with special reference to enzymatic procedures. Clin. Chem. Acta 1977; 75:243–51.

18. Ludwig M, Wohn K D, Schleuning, and Olek D. Allellic dimorphism in the human tissue type plasminogen activator (TPA) gene as a result of an Alu insertion/deletion event. Hum Genet 1992; 88:388–392.

19. Miettinen O S. Proportion of disease caused or prevented by a given exposure, trait or intervention. Am J. Epidemiol 1974;99:325–32.

20. Benham F J, Spurr N, Povey S, Brinton B T, Goodfellow P N, Solomon E, Harris T J R. Assignment of tissue type plasminogen activator to chromosome 8 in man and identification of a common restriction length polymorphism within the gene. Mol Biol Med 1984;2:251–9.

21. Dano K. Andreasen P A, Grondahl-Hansen J, Kristensen P, Nielsen L S, Skriver L. Adv. Cancer Res. 1985;44:139–266.

22. Saksela O, Rifkin D B. Cell Physiol 1988; 4:93–126.

23. Iacoviello L., De Knijff P., amore C., Kluft C. and Donati M. B., In Fibrinolysis: International Journal of fibrinolysis, Thrombolysis and Extracellular Proteolysis Abstracts and Invited lectures of the XIIth International Congress on Fibrinolysis, Leuven, Belgium, Sep. 18–22, 1994, volume 8, supplement 1, 1994: Ed. H. R. Lijnen, poster presentation p3 Physiological and population studies 49; 136 t-PA and family history of thrombosis in AMI patients from GISSI trial: Biochemical and genetic aspects.

24. Erikkson, P. et al, Proc. Natl. Acad. Sci USA, Vol. 92, pp. 1851–1855, March 1995, Medical Sciences.

25. ISIS-3 (third international study of infarct survival) collaborative group. ISIS-3: a randomised comparison of streptokinase vs tissue plasminogen activator vs anistreplase and of aspirin plus heparin vs aspirin alone among 41299 cases of suspected acute myocardial infarction. Lancet 1992; 339: 753–70.

26. The GUSTO investigators. An international randomized trial comparing four thrombolytic strategies for acute myocardial infarction. New Engl J Med 1993; 329: 673–82)

27. Degen S. J. F., Rajput B, Reich E (1986) The human tissue type plasminogen activator gene J. Biol. Chem. 261: 6972–6985

TABLE 1

Baseline characteristics of the study population. D/D = homozygote for the deletion; I/D = heterozygote for the insertion/deletion; I/I = homozygote for the insertion polymorphism.

|  | D/D (n = 75) | I/D (n = 138) | I/I (n = 138) | P |
| --- | --- | --- | --- | --- |
| Age (years) | 71,3? | 72,9 | 72,0 | 0,42 |
| Gender (% female) | 55 | 52 | 53 | 0,90 |
| smoking (% yes) | 18 | 19 | 19 | 0,97 |
| Total cholesterol (mmol/1) | 6,38 | 6,45 | 6,45 | 0,92 |
| HDL cholesterol (mmol/1) | 1,32 | 1,30 | 1,30 | 0,43 |
| systolic blood pressure (mmHg) | 135 | 141 | 141 | 0,17 |
| Diastoloc blood pressure (mmHg) | 75 | 73 | 73 | 0,56 |
| Body mass index (kg/m$^2$) | 26,7 | 26,2 | 26,2 | 0,56 |
| Control subjects (number) | 53 | 76 | 76 |  |
| Case subjects (number) | 22 | 62 | 62 |  |

TABLE 2

Relative risk of myocrdial infarction by presence of the insertion.

|  | D/D * | D/I | I/I |
| --- | --- | --- | --- |
| Crude risk | 1 | 1,44 (0,81–2,65) | 1,95 (1,07–3,57) |
| Adjusted for age and gender | 1 | 1,40 (0,78–2,53) | 1,96 (1,05–3,46) |
| Adjusted for age, gender and other risk factors[+] | 1 | 1,42 (0,74–2,73) | 2,04 (1,03–4,03) |

* Reference risk (i)
[+]Risk factors include smoking (yes/no), total cholesterol (mmol/l), HDL cholesterol (mmol/l), systolic blood pressure (mmHg), diastolic blood pressure (mmHg), and body mass index (kg/m$^2$).

We claim:

1. A method for diagnosing an increased risk of a thrombus associated disease in an individual, comprising isolating nucleic acid from said individual, and analyzing the nucleic acid for the presence of a t-PA (tissue plasminogen activator) Alu-h I allele, wherein detection of said t-PA Alu-h I allele is indicative of such increased risk.

2. The method of claim 1, wherein prior to analyzing the nucleic acid, the nucleic acid is amplified.

3. The method of claim 2, wherein the nucleic acid is DNA.

4. The method of claim 2, wherein the nucleic acid is RNA.

5. A diagnostic kit for determining an increased risk of thrombus associated disease, comprising oligonucleotide primers that will amplify the region encompassing the t-PA Alu-h I allele.

6. The kit of claim 5, further comprising a detectable marker for the amplification product.

7. The kit of claim 6, wherein the detectable marker comprises a oligonucleotide probe provided with a label.

* * * * *